United States Patent [19]

Audet

[11] 4,051,560

[45] Oct. 4, 1977

[54] BOWEL MOVEMENT ENERGIZER SYSTEM

[76] Inventor: Francois Audet, 5010 Fossambault Boulevard, St. Catherine, Portneuf, Canada

[21] Appl. No.: 728,935

[22] Filed: Oct. 4, 1976

[51] Int. Cl.² ............................................. A47K 17/00
[52] U.S. Cl. ............................................... 4/1; 4/237;
128/24 R; 128/33; 128/49; 272/132
[58] Field of Search ............................. 4/237, 1, 234;
128/24 R, 25, 33, 48, 49, 70; 272/58

[56] References Cited

U.S. PATENT DOCUMENTS

| | | | |
|---|---|---|---|
| 2,256,994 | 9/1941 | Warshaw | 4/237 |
| 2,598,577 | 5/1952 | Mattison | 4/237 |
| 3,004,534 | 10/1961 | Gottberg | 4/237 X |
| 3,244,168 | 4/1966 | Bayard | 128/33 |
| 3,824,991 | 7/1974 | Whitaker | 128/24 R |

Primary Examiner—Henry K. Artis

[57] ABSTRACT

A system adapted to energize bowel movement of a person sitting on a toilet bowl and including a pair of exerciser units operatively mountable on the opposite side of the toilet bowl and to require lateral rocking movement of the user for actuation. Each exerciser unit includes a bracket securable to the edge of a toilet bowl with an outward base portion, a rotary member rotatably secured to the base portion, and a handle connected to the rotary member and displaceable up and down to require lateral rocking movement of the user for actuation. In embodiments of the invention, the exerciser units include each a rotation-resistant device which is adjustable to adapt the resistance to rotation to the strength and/or desire of the user.

12 Claims, 7 Drawing Figures

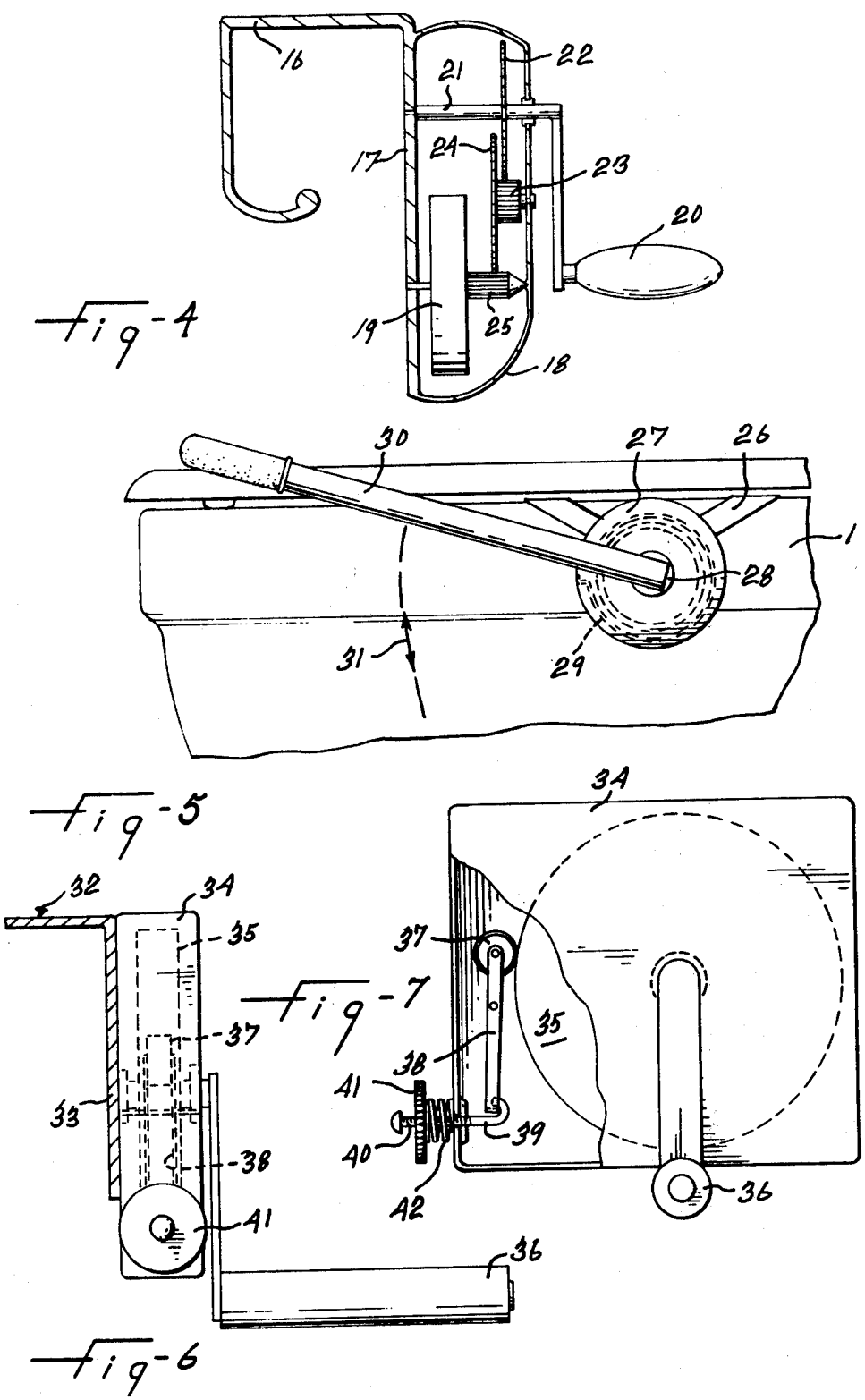

BOWEL MOVEMENT ENERGIZER SYSTEM

This invention relates to a system for energising bowel movement and, more particularly, to a bowel movement energiser system of the type including a pair of exerciser units fixable on opposite sides respectively of a toilet bowl and whose actuation promotes bowel movement.

It is known that the bowel movement is greatly assisted by movements of the body. However, for constipated persons and in particular for elderly and handicapped persons, the current or normal physical activities are not sufficient to induce the required bowel movement. It has so far been proposed to associate some mechanism to the toilet bowl to produce movements of the toilet seat. However, such mechanism is rather complex and requires some strong motor to rock the toilet seat with a person seated thereon.

According to the present invention, the bowel movement energiser system uses exercisers which are actuated by the user and are fixed on opposite sides of the toilet bowl to require a lateral rocking movement of the body for actuation by a person sitting on the toilet bowl. By experience, it has been found that such lateral rocking is very efficient to energise the bowel movement.

It is a general object of the present invention to provide a bowel movement energiser system which is simple, inexpensive and efficient, and which is easy to operate by the user.

It is another object of the present invention to provide a bowel movement energiser system which includes a pair of exerciser units operatively securable on opposite sides of a toilet bowl to require lateral rocking of the user's body for actuation thereof.

It is a further object of the present invention to provide a bowel movement energiser system wherein a pair of exerciser units are operatively mounted on opposite sides of a toilet bowl and include a rotatable handle whose resistance to rotation is adjustable according to the requirement of any particular user.

The foregoing and other objects and advantages of the present invention will be better understood with reference to the following detailed description of preferred embodiments thereof, which are illustrated, by way of example, in the accompanying drawings, wherein:

FIG. 4 is a cross-sectional elevation view of an exerciser unit according to a second embodiment of the present invention;

FIG. 5 is a side elevation view of an exerciser unit according to a third embodiment of the present invention and shown in operative position on one side of a toilet bowl;

FIG. 6 is an elevation view of an exerciser unit according to a fourth embodiment of the present invention; and FIG. 7 is a side elevation view of the exerciser unit of FIG. 6 with part of the housing broken away to show internal parts.

The present invention defines a system associated to a toilet bowl to energise bowel movement. This system includes a pair of exerciser units which are operatively secured to the opposite sides respectively of the toilet bowl 1 in transverse alignment with the trunk or spine of the person sitting on the toilet bowl.

Figure 1:
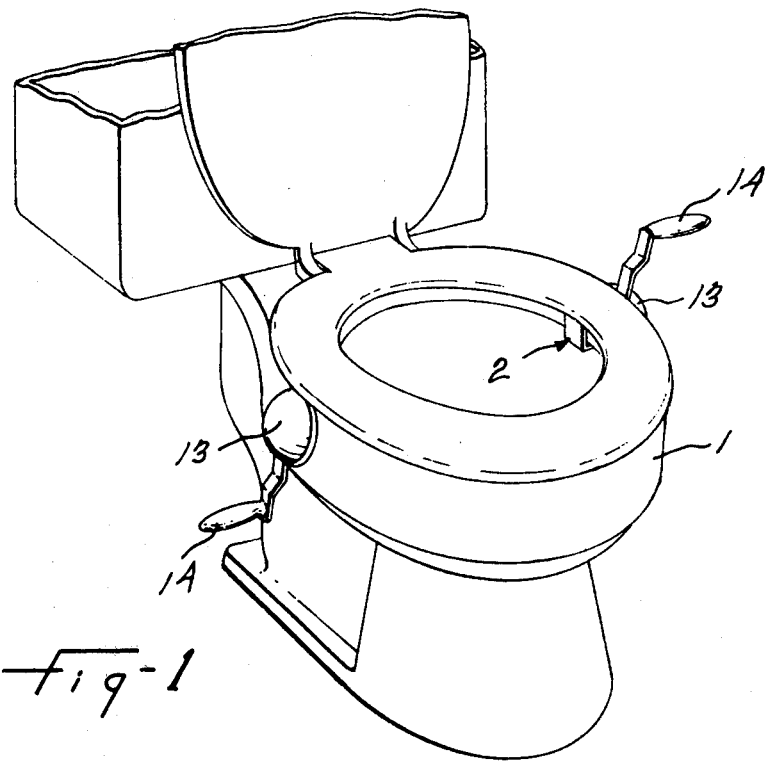
FIG. 1 is a perspective view of a toilet bowl with a bowel movement energiser system with exerciser units according to a first embodiment of the present invention.
Figure 2:
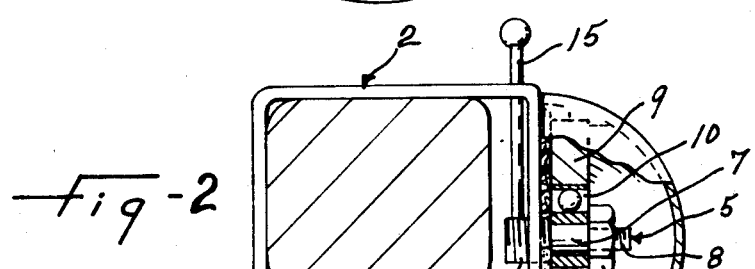
FIG. 2 is a cross-sectional elevation view of one exerciser unit forming part of the system of FIG. 1.
Figure 3:
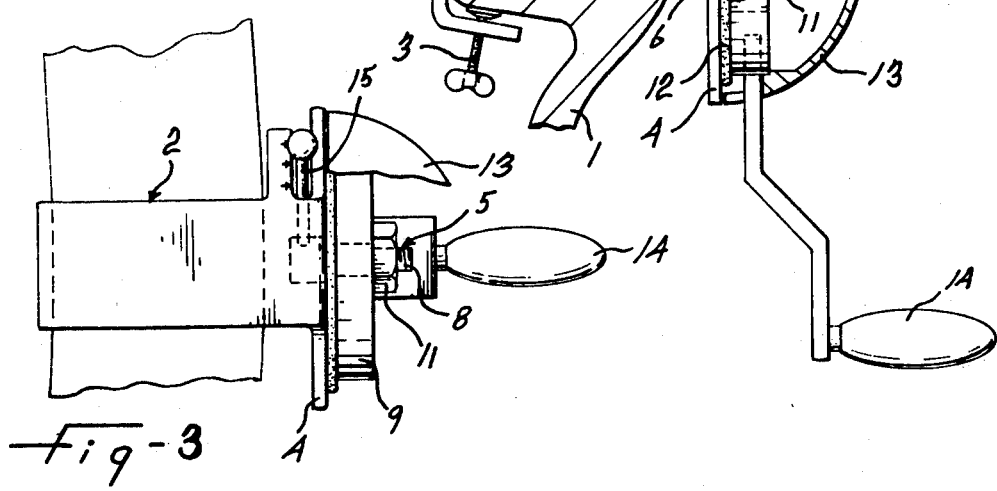
FIG. 3 is a top view of the exerciser unit of FIG. 2 with part of the housing broken away.

The exerciser units of the first embodiment, as shown in FIGS. 1, 2, and 3, include each a bracket 2, of appropriate profile, to engage the edge of a toilet bowl 1. The bracket 2 is fixed to the edge of the bowl by a screw 3, or any other suitable expedient. Each bracket 2 includes a base portion 4 which extends upright outside the toilet bowl. A shaft 5 is fixed to the base portion 4 by a threaded portion 6 adjustably screwed in the base portion. The shaft 5 also includes a journal portion 7 and a smaller threaded portion 8. A disc, or wheel 9, is rotatably mounted on the journal portion 7 of the shaft 5, by a ball bearing 10. A nut 11 is screwed on the smaller threaded portion 8 and forms an axial abutment holding the wheel 9 against axial displacement thereof away from the larger threaded portion 6. A pad 12, of frictional material, is engaged between the wheel 9 and the base portion 4. A dome-shaped housing 13 is firmly fixed to the wheel 9 for bodily rotation therewith. A handle 14 is fixed by an arm to the wheel 9 to rotate the latter about the axis defined by the shaft 5. This axis extends transversely relative to the bowl 1. An adjustment arm 15 is fixed to the larger threaded portion 6 of the shaft 5 to rotate the latter and thus axially adjust the shaft and, thus, the pressure of engagement of the wheel 12 against the pad 9. Consequently, the rotation resistance of the wheel 9 may be adjusted by actuation of the lever 15.

The exerciser unit according to the second embodiment illustrated in FIG. 4, includes a bracket 16 with a base portion 17 to engage over the edge of a toilet bowl 1 with the base portion 17 outward of the toilet bowl. A casing, or housing 18, is fixed against the base portion 17. A flywheel 19 is rotatably mounted in the casing 18 about an axis extending transversely of the toilet bowl. A handle 20 is fixed to a shaft 21 and rotates the latter about an axis parallel to the axis of the flywheel 19. A gear train including gears 22, 23, 24, and 25 drivingly interconnects the shaft 21 and the flywheel 19.

The exerciser unit illustrated in FIG. 5 includes a bracket 26, also defining an outward base, not shown. A casing, or housing 27, is fixedly secured to the base portion of the bracket 26 and rotatively carries a shaft or rotary member 28 in cooperation with the base portion. A coil spring 29 is mounted in the housing 27 and fixed at the outer end to this housing and at the inner end to the shaft 28. A handle, or hand lever 30, is rigidly fixed to the shaft or rotary member 28.

The hand lever 30 is thus displaceable up and down, as shown by the arrow 31, with and against the action of the spring 29.

The exerciser unit shown in FIGS. 6 and 7 includes a mounting bracket 32 operatively engageable with the edge of a toilet bowl 1 and including an outward base portion 33. A casing 34 is fixed against the base portion 33. A wheel 35 is rotatably mounted in the casing 34 for rotation about an axis extending transversely of the toilet bowl 1. A handle 36 is fixed to the shaft of the wheel 35 to cause rotation of the latter.

A rotation-resistant device is operatively connected to the wheel 35 and adapted to adjust the resistance to rotation of the latter. This rotation-resistant device includes a rotation-resistant idler wheel 37 rotatably mounted on one end of a lever 38 and rolling against the circumferential surface of the wheel 35. The rotation-resistant device includes an adjustable hook 39 hooked to the other end of the lever 38 and having a threaded shank 40 outwardly and slidably projecting from the casing 34. An adjustment wheel 41 is screwed on the threaded shank 40 and a spring 42 is positioned between the adjustment wheel 41 and the casing 34. Thus, the screwing or unscrewing of the adjustment wheel, 41 along the threaded portion of the hook 39, axially adjusts the latter under the bias of the spring 42. A resultant pivoting of the lever 38 is thus produced with a resultant lower or higher pressure of the roller 37 against the wheel 35. The resistance to rotation of the wheel 35 may thus be adjusted by appropriate rotation of the adjustment wheel 41.

According to the present invention, a pair of exerciser units fixed on the opposite sides of a toilet bowl 1 and are cyclically operated with the handles diametrically opposite each other, as shown in FIG. 1, to produce a lateral rocking of the user's body.

It must be understood that other embodiments of the invention and changes to the details of construction are possible without departing from the spirit and scope of the invention as defined in the appended claims.

What I claim is:

1. A bowel movement energiser system adapted for operation by a person sitting on a toilet bowl, this energiser system comprising a pair of exerciser units operatively securable to the opposite sides respectively of the toilet bowl in transverse alignment with the trunk of the person sitting on the toilet bowl, each exerciser unit including a bracket fixedly securable to the upper edge of the toilet bowl and having a base portion outwardly positioned with respect to the toilet bowl, a cyclic movement mechanism mounted on said base portion, and a handle operatively connected to said cyclic movement mechanism and operatively displaceable up and down laterally outward of said toilet bowl for actuation of the corresponding cyclic movement mechanism.

2. A bowel movement energiser system as defined in claim 1, wherein said cyclic movement mechanism includes a rotary member and the latter and said handle are rotatably mounted on said base portion.

3. A bowel movement energiser system as defined in claim 2, further including a rotation-resistant device connected to the rotary member of each exerciser unit and imposing resistance to rotation by the person actuating the corresponding handle.

4. A bowel movement energiser system as defined in claim 3, wherein said rotation-resistant device includes a rotation-resistant member engaging the corresponding rotary member and an adjustable member connected to the rotation-resistant member and constructed and arranged to vary the resistance to rotation of the latter and thus the effort required to rotate the corresponding handle and, concurrently, to produce lateral rocking movement of the body by the user.

5. A bowel movement energiser system as defined in claim 4, wherein said rotary member and said handle are rotatable each about an axis extending transversely to said bowl.

6. A bowel movement energiser system as defined in claim 5, wherein said rotary member is rotatably mounted adjacent said base portion and axially displaceable toward the latter, said rotation-resistant member is a pad of frictional material mounted between said base portion and said rotary member, and said adjustable member engages said rotary member and axially adjust the frictional engagement of the latter with the pad of frictional material.

7. A bowel movement energiser system as defined in claim 6, wherein said adjustable member constitutes a shaft rotatably carrying said rotary member, defining the rotation axis of the latter, and adjustably screwed in said base portion, said rotary member is rotatably mounted on said shaft, an axial abutment device axially holds said rotary member against axial displacement on said shaft away from said pad of frictional material, said handle is rigidly fixed to said rotary member for bodily rotation of the latter therewith, and an adjustment arm is fixed to said shaft for rotation and axial adjustment thereof by screwing or unscrewing of the same in said base portion.

8. A bowel movement energiser system as defined in claim 2, wherein said rotary member constitutes a flywheel and a gear train rotatively connects said handle to said flywheel.

9. A bowel movement energiser system as defined in claim 8, wherein a casing is fixed to said base portion and encloses said flywheel and said gear train cooperatively with the base portion, said rotary member and said handle are rotatable about parallel axes extending transversely to said bowl.

10. A bowel movement energiser system as defined in claim 2, wherein a coil spring is fixedly secured at one end to said rotary member and at the other end relative to the base portion, and said handle engages said rotary member and rotates the latter back and forth with and against the action of the coil spring about a transverse axis relative to said bowl.

11. A bowel movement energiser system as defined in claim 5, wherein said rotation-resistant device includes a lever, said rotation-resistant member is mounted on said lever and displaceable therewith toward rotation-resistant engagement with the rotary member and said adjustable member is connected to said lever and adapted to adjustably pivot the latter toward adjusted rotation-resistant engagement with the rotary member.

12. A bowel movement energiser system as defined in claim 11, wherein said rotary member constitutes a wheel having a circumferential surface, said handle is fixed to said wheel for rotation therewith about a common axis, said rotation-resistant member is an idler wheel rotatable on said one end of the lever against said circumferential surface, said adjustable member constitutes a hook engaging the other end of the lever and having a threaded portion, an abutment member is adjustably screwable along the threaded portion of the hook, and a spring engages said adjustably screwable abutment member and operatively biases the hook and said lever toward rotation-resistant engagement of said idler wheel with said circumferential surface.

* * * * *